(12) United States Patent
Ohresser

(10) Patent No.: US 7,192,734 B2
(45) Date of Patent: Mar. 20, 2007

(54) METHOD OF TESTING FOR THE PRESENCE OF MICROORGANISMS IN A GASEOUS ENVIRONMENT COMPRISING HYDROGEN PEROXIDE

(75) Inventor: Serge Ohresser, Still (FR)

(73) Assignee: Millipore Corporation, Billerica, MA (US)

( * ) Notice: Subject to any disclaimer, the term of this patent is extended or adjusted under 35 U.S.C. 154(b) by 335 days.

(21) Appl. No.: 10/305,831

(22) Filed: Nov. 27, 2002

(65) Prior Publication Data

US 2003/0148415 A1 Aug. 7, 2003

(30) Foreign Application Priority Data

Jan. 18, 2002 (FR) .................................. 02 00608

(51) Int. Cl.
*C12Q 1/04* (2006.01)
(52) U.S. Cl. ...................................................... 435/34
(58) Field of Classification Search ................ 435/34, 435/262, 262.5, 859, 862, 875, 883, 884, 435/885
See application file for complete search history.

(56) References Cited

U.S. PATENT DOCUMENTS

| | | | | |
|---|---|---|---|---|
| 3,514,278 A | * | 5/1970 | Brink, Jr. ..................... | 504/150 |
| 4,528,269 A | | 7/1985 | Sandine et al. ............... | 435/34 |
| 5,266,096 A | * | 11/1993 | Slavensky ........................ | 71/6 |
| 6,015,706 A | * | 1/2000 | Kim et al. ................ | 435/252.1 |

FOREIGN PATENT DOCUMENTS

| | | |
|---|---|---|
| GB | 1 554 193 | 10/1979 |
| WO | 99/02650 | 1/1999 |

OTHER PUBLICATIONS

PDR Health . http//: www.pdrhealth.com/drug, dated Jun. 5, 2005, pp. 1-3.*

Copy of the Search Report dated Dec. 2, 2002.
Decontamination with vaporized hydrogen peroxide is effective against *Mycobacterium tuberculosis*. Lett. Appl. Microbiol 2005; 40(6): 448-452.
Efficacy of vaporized hydrogen peroxide against exotic animal viruses. Appl. Environ. Microbiol. Oct. 1997; 63(10): 3916-3918.
Comparison of ion plasma, vaporized hydrogen peroxide, and 100% ethylene oxide gas sterilizer. Infect Control Hosp Epidemiol Feb. 1996; 17(2): 92-100.
Nuncbrand—Petri Dishes (1-Page), date not available at website.
BD Biosciences—BD Falcon BioDish XL—5-Pages, date not available at website.
SARSTEDT—Petri dishes for bacteriology—pp. 51 and 117, date not available at website.
Serva.de/products—Nutrient Broth (Standard II Nutrient Broth) 15g for 1 liter medium—1 Page, date not available at website.
Emdchemicals—Standard I Nutrient Broth—2 Pages, date not available at website.
Millipore Corporation; Serge Ohresser, Ph.D.; "The Effect of Residual VHP on Microorganism Recovery when Performing Air Monitoring in Isolators"—8-Pages, date not available at website.

* cited by examiner

*Primary Examiner*—Jon Weber
*Assistant Examiner*—Kailash C. Srivastava
(74) *Attorney, Agent, or Firm*—Nields & Lemack

(57) ABSTRACT

The invention relates to a method of testing for the presence of microorganisms in a gaseous environment comprising hydrogen peroxide, comprising the following steps:
(i) bringing the gaseous environment comprising the hydrogen peroxide into contact with an agar growth medium, comprising a salt of pyruvic acid,
(ii) placing the growth medium in an environment favoring the development of colonies of microorganisms;
(iii) determining the presence of colonies of microorganisms which may have developed during step (ii).

The invention also relates to a cassette containing an agar growth medium comprising a salt of pyruvic acid.

12 Claims, 6 Drawing Sheets

METHOD OF TESTING FOR THE PRESENCE OF MICROORGANISMS IN A GASEOUS ENVIRONMENT COMPRISING HYDROGEN PEROXIDE

This application claims priority to French Patent Application 0200608, filed Jan. 18, 2002.

The present invention relates to a method of testing for the presence of microorganisms in a gaseous environment comprising hydrogen peroxide, as well as to cassettes containing an agar growth medium adapted to be implemented in this method.

It is well known that, for the implementation of certain industrial processes, in particular in the pharmaceutical industry, various actions or manipulations must be performed in confined preparation zones, such as isolators, separated from the outside world and rendered aseptic.

It is common, in order to test the asepsis of the gaseous environment, generally air, existing in these confined zones, to take a gaseous sample which may contain microorganisms, bacteria, yeasts or moulds, to apply them to a layer of agar contained in a receptacle or cassette, and then to leave the receptacle to incubate at temperature, for a predetermined time, such that these microorganisms form colonies that are visible to the naked eye. It is thus possible to visualize, count, and, where appropriate, identify the colonies of microorganisms present in the analyzed air.

To sterilize these confined zones, it is possible to use in particular hydrogen peroxide in gaseous form. Hydrogen peroxide, introduced into a gaseous environment for the purposes of asepsis, will be referred to herein as "exogenous hydrogen peroxide"

Thus, in particular for the sterilization of isolators, three steps are generally carried out:
- a dehumidifying step for drying the ambient air of the isolator, during a period of about 15 to 20 minutes;
- a gassing step to bring a certain quantity of hydrogen peroxide into contact with the internal environment of the isolator, and
- an aeration step, for eliminating the hydrogen peroxide.

At the end of this sterilization cycle, a test of the level of microorganisms is carried out by sampling the air within the isolator to be sure of its sterility.

Nevertheless, despite the precautions taken, in particular during the aeration step, the applicant has found that the gaseous environment may contain significant residual quantities of hydrogen peroxide, able to distort the results of the test for the level of microorganisms and thereby lead to false negatives.

The applicant therefore sought to develop a method for solving the problem of testing for the presence and/or level of microorganisms in a confined zone, in the presence of a significant quantity of hydrogen peroxide, to avoid any risk of false negatives.

It is also known that microorganisms having undergone stress may enter into a state in which they are still active, but are unable to multiply on a growth medium. More particularly, due to the stress, these microorganisms lose their catalase and superoxide dismutase activity. Thus, when they are placed on a rich nutritive medium, they no longer have means available for eliminating peroxides, and in particular hydrogen peroxide, which they produce themselves when they are placed in culture, or which are formed by photochemical reaction or auto-oxidation of certain compounds present in the growth medium. In the description which follows, the term "endogenous hydrogen peroxide" will be used to refer to such hydrogen peroxide formed by the microorganisms themselves or as a result of reactions involving the compounds making up the growth medium.

Certain authors have proposed the addition to the growth medium of compounds known to break down the endogenous hydrogen peroxide, such as catalases, or non-enzyme compounds such as α-ketoglutaric acid, 3,3'-thiodipropionic acid, and sodium pyruvate, with the objective of identifying and/or counting the microorganisms present in an environment, despite the stress phenomenon.

Thus, R. M. Lee et al, in *Journal of Food Protection, Vol.* 52, Feb. 1989, pp 119–121, described the addition of increasing amounts of sodium pyruvate to an agar growth medium, to increase the recovery of coliform bacteria from samples of food products and water.

J. P. Calabrese et al., in *Can. J. Microbiol., Vol.* 36, 1990, pp 544 –550, have shown that the addition of catalase, of sodium pyruvate or their combination, make it possible to increase the recovery of coliform bacteria stressed by acidic water. S. Czechowicz et al., in *International Journal of Food Microbiology* 33 (1996), pp 275–284, and Y. Mizunoe et al., in *Arch Microb.* (1999) 172: 63–67, have used catalases, α-ketoglutaric acid, 3,3'-thiodipropionic acid, and sodium pyruvate to increase the recovery of *Escherichia coli* degraded either by food deprivation or by a thermal stress.

With a view to solving the problem which applicant had identified, as mentioned above, the applicant initially envisaged the use of an agar growth medium, supplemented with catalase.

However, applicant then encountered a difficulty, which the articles cited above do not appear to have met, and which appears to be specific to the problem of testing for the presence and level of microorganisms in a gaseous environment comprising exogenous hydrogen peroxide. Thus, following certain of the authors cited above, the applicant initially added catalase to the growth medium used. It proved to be the case, however, that the breakdown of the hydrogen peroxide by the catalase led to the formation of significant quantities of oxygen bubbles at the surface and within the agar of the growth medium, and these bubbles made visualization of the microorganism colonies very difficult. Furthermore, the use of catalase in quantities up to 8000 IU/plate (that is to say per agar growth medium) only enabled a relatively low level of microorganism recovery, as defined hereinafter, of the order of 60%. Higher levels of catalase were not envisaged by the applicant. This was because it was considered that this would lead to the formation of such a quantity of oxygen bubbles that the visualization of the microorganism colonies would be made still more difficult, or even impossible. In addition, catalases are onerous products, such that their use in too large quantities would be prohibitive, from an economic point of view, with no guarantee that this would improve the level of recovery.

The applicant has continued with its research and has been able to solve the problem raised above by means of the method constituting a first aspect of this invention.

Thus the invention consists in a method of testing for the presence of microorganisms in a gaseous environment comprising hydrogen peroxide, characterized in that the following steps are implemented:
(i) bringing the gaseous environment comprising the hydrogen peroxide into contact with an agar growth medium, comprising a salt of pyruvic acid.
(ii) placing the growth medium in an environment favoring the development of colonies of microorganisms;
(iii) determining the presence of colonies of microorganisms which may have developed during step (ii).

The salt of the pyruvic acid makes it possible to carry out the test for the presence of microorganisms present in a gaseous environment, without risk of false negative.

Furthermore, and in contrast with what it has been possible to observe by the implementation of catalase, the salt of pyruvic acid does not hinder the determination of the colonies of microorganisms and permits a high level of recovery.

This was unexpected since certain of the authors mentioned above, in order to enable the growth of colonies of microorganisms in the presence of endogenous hydrogen peroxide, used indiscriminately a growth medium to which had been added a catalase or sodium pyruvate.

The invention will now be described in detail by means of the description which follows and the drawings.

Figure 1:
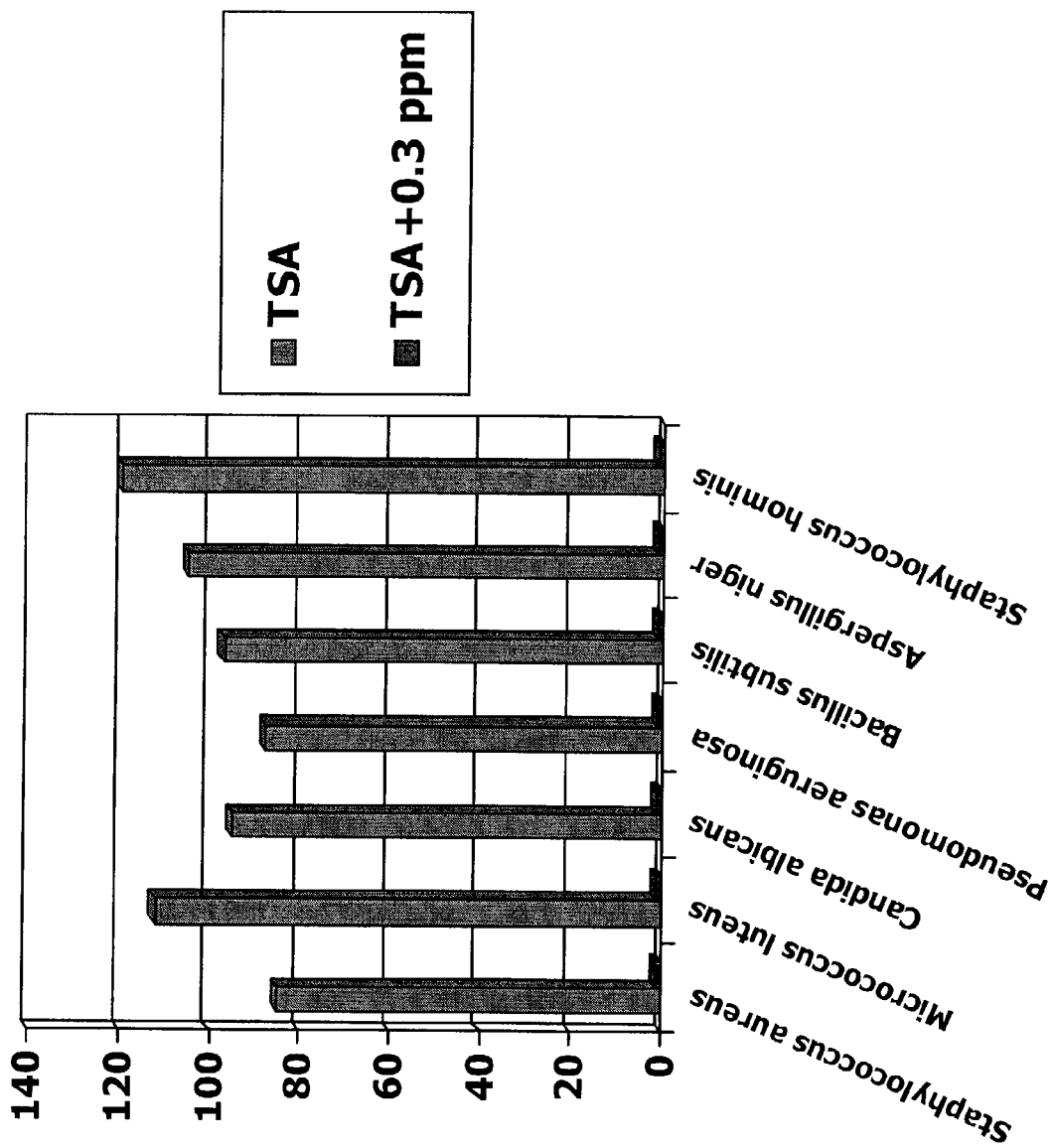
FIG. 1 represents a bar chart showing the effect of a concentration of 0.3 ppm of hydrogen peroxide on the recovery level of the microorganisms.

In the sense of the present invention, the expression "level of recovery of the microorganisms" is understood to mean the ratio between, on the one hand, the number of colonies of microorganisms formed (cfu) on an agar growth medium previously exposed to a particular gaseous environment, to which an aqueous suspension has been applied containing a known number of microorganisms (cfu), and, on the other hand, the number of colonies of microorganisms formed (cfu) on an agar growth medium after application of the same aqueous microorganism suspension, the agar growth medium having been maintained beforehand in a sterile atmosphere and not having been exposed to the particular gaseous environment, all other things being equal.

The hydrogen peroxide is generally vaporized or sprayed in the gaseous environment.

Surprisingly It has been found by the Applicant that the inhibition of microorganism growth is higher when the hydrogen peroxide is sprayed than when it is vaporized.

Typically, the gaseous environment comprising hydrogen peroxide is ambient air, in particular ambient air present in a confined zone, such as an isolator.

The level of hydrogen peroxide in the gaseous environment may be between 1 ppm (part per million) and 400 ppm, preferably between 0.1 ppm and 20 ppm, more preferably between 0.2 ppm and 10 ppm. One ppm of hydrogen peroxide corresponds to 1.4 mg of hydrogen peroxide/$m^3$.

The agar growth medium may comprise, in addition to the agar, a product of enzyme digestion of a protein, such as casein, a plant flour, or yeast extracts.

The agar growth medium may consist of a TSA (Tryptic Soy Agar) medium comprising:

| | |
|---|---|
| pancreatic digest of casein | 15 g |
| papaic digest of soybean meal | 5 g |
| sodium chloride | 5 g |
| agar | 15 g |
| water ams | 1000 ml |

An appropriate TSA growth medium is sold by the company DIFCO under the reference 236950.

The agar growth medium may comprise 0.1 to 3% by weight, and preferably 0.5% to 1.5% by weight, of at least one pyruvic acid salt.

The pyruvic acid salt, able to be implemented in the context of the present invention, may be a salt of an alkali metal, such as that of sodium or potassium, a salt of an alkaline earth metal, such as that of calcium or magnesium, or a mixture of two or more of these salts. Preferably sodium pyruvate is used.

It is also possible to apply the method of the present invention when particular intensive sterilization is sought through the use of high or even very high levels of hydrogen peroxide, which can be from 15 ppm up to 300 ppm, or even 400 ppm. Such high levels of hydrogen peroxide are also found when sterilization cycles are carried out in shorter time than required. This occurs when the users do not respect the instructions for carrying out said sterilization cycles or if the user does not properly monitor the content of the peroxide hydrogen amount.

In such conditions, where high levels of hydrogen peroxide are present in the gaseous environment, large amounts of pyruvic acid salt in the agar growth medium can be successfully carried out in accordance with the method of the present invention, to enable microorganism growth recovery. The amount of pyruvic acid salt can thus be comprised between more than 1% and 5%, preferably between 3% and 5% by weight.

The possible use of such a large amount of pyruvic acid salt was unexpected since it was believed by one skilled in the art that this should lead to inhibit rather than favor microorganism growth recovery.

It was still more unexpected that the growth of microorganism could take place with such amounts of pyruvic acid salt in the presence of high concentration of hydrogen peroxide, which, as seen above, also inhibits microorganism growth recovery.

The agar growth medium preferably has a thickness of 1 to 20 mm, and preferably 5 to 8 mm.

The growth medium may be prepared in a manner known to the person skilled in the art, simply by mixing its constituents.

According to the method of the invention, the surface of the agar growth medium is advantageously brought into contact with a controlled flow of said gaseous environment comprising hydrogen peroxide, said flow having a substantially constant rate of flow. By applying a flow thus controlled for a predetermined period of time, it is possible to choose the volume of air, or of another gaseous environment, that it is desired to apply to the surface of the agar growth medium and thereby render the method of the invention reproducible.

Such a controlled flow may be achieved by means of a sampling apparatus comprising means for air suction, such as a pump, as well as means for holding a cassette or a box in which the agar growth medium has been set, so as to permit the air to be brought into contact with the surface of the agar.

Such a device is described in the French patent applications No. 98 07299 and 98 05166 in the name of Millipore S. A., to which reference is made in the present description. Such a device is also sold by the company Millipore, under the trade mark M Air T™ Isolator.

The culture of the growth medium having been brought into contact with the gaseous environment may be implemented in any appropriate device, such as a temperature-controlled incubator.

Generally, at the end of step (iii) of the method of the invention, the number of colonies is counted and/or the nature of the microorganisms which make up the colonies is identified, by means known to the person skilled in the art.

To facilitate the counting of the colonies, cassettes or box of grid form can be used, which are filled with the agar growth medium.

According to another aspect of the invention, this consists of a cassette or a box provided with means for attachment to an apparatus for sampling air or another gaseous environment, as described above, and in which an agar growth medium has been set comprising a salt of pyruvic acid.

Such a cassette, comprising a conventional agar growth medium, is known per se. It is sold by the company Millipore, under the trade mark M air T™.

A cassette according to the invention may be implemented in the method described above.

The object of the following examples is to illustrate the present invention.

EXAMPLE 1

Not According to the Invention

In order to test for the influence of traces of gaseous hydrogen peroxide on the formation of colonies of different microorganisms, a sample of 1 $m^3$ of air was first of all taken in a laminar air flow hood serving as a sterile environment and being free from hydrogen peroxide. The air sampled in this manner had been impacted on the surface of a TSA growth medium, sold by the company DIFCO under the reference 236950.

The surface of the growth medium was spread with an aqueous suspension comprising a predetermined number of microorganisms.

The TSA growth media were next placed in a temperature-controlled incubator to enable the growth of the colonies of microorganisms.

This test was repeated, but with a TSA growth medium impacted with 1 $m^3$ of air comprising 0.3 ppm of sprayed hydrogen peroxide.

The results obtained are represented in FIG. 1, where the x-axis represents the nature of the microorganisms which developed on the surface of the agar growth medium and the y-axis represents the level of recovery, that is to say the ratio between the number of cfu determined in the presence of hydrogen peroxide and the number of cfu determined in the sterile environment.

The results obtained show that a low hydrogen peroxide content may lead to inhibiting of the formation of the colonies of microorganisms and thus lead to false negatives.

EXAMPLE 2

Not According to the Invention

Example 1 was reproduced but with the use of 1 $m^3$ of air comprising 3 ppm of hydrogen peroxide (instead of 0.3 ppm) which are impacted this time on TSA growth media to which increasing levels of a catalase (0 to 8000 IU/plate) were added. The only microorganism used was *Staphylococcus aureus*.

Figure 4:
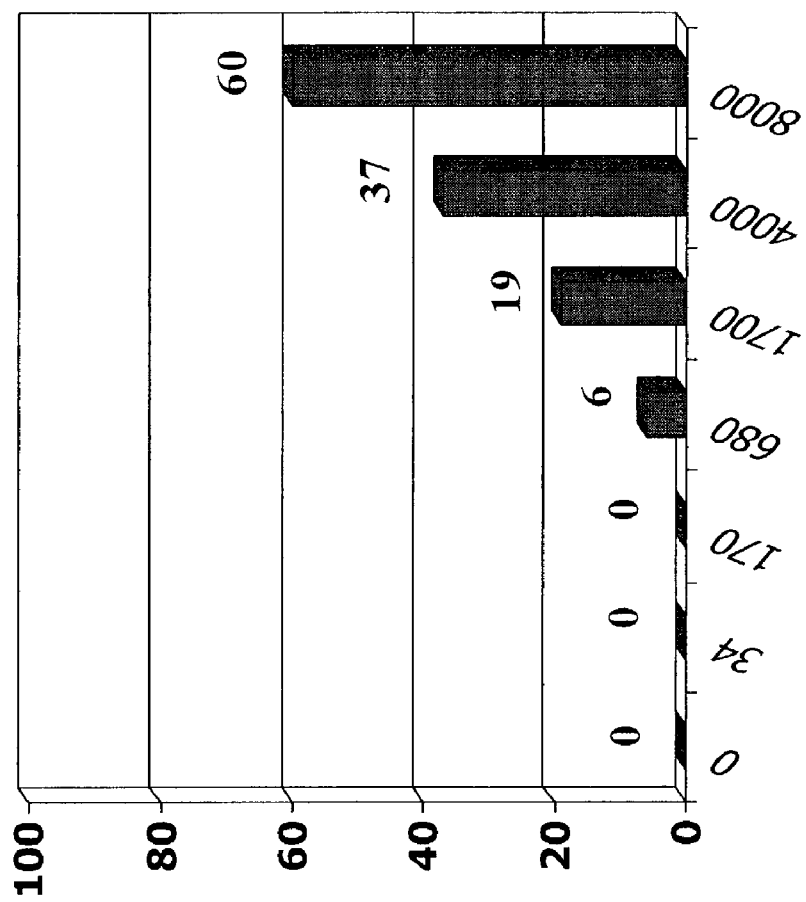
FIG. 4 represents a bar chart showing the effect of a catalase in increasing concentration in the presence of 3 ppm of hydrogen peroxide on the recovery level of the microorganisms.

The results obtained are shown in FIG. 4, in which the x-axis represents the amount of catalase and the y-axis represents the level of recovery.

It is found that catalase, used at high doses (8000 IU/plate) enables a maximum level of recovery of 60%, which is significantly less than the results obtained with the method of the invention, which led to a level of recovery of close to 120% for *Staphylococcus aureus*.

Furthermore, catalase gave rise to the formation of oxygen bubbles which made the counting of the cfu's difficult.

EXAMPLE 3

Example 1 was reproduced but with the use of 1 $m^3$ of air comprising 8 ppm (instead of 0.3 ppm) of hydrogen peroxide vapour (instead of sprayed hydrogen peroxide which was impacted, firstly, on a TSA growth medium, then, secondly, on the TSA medium to which 1% by weight of sodium pyruvate was added.

Figure 2:
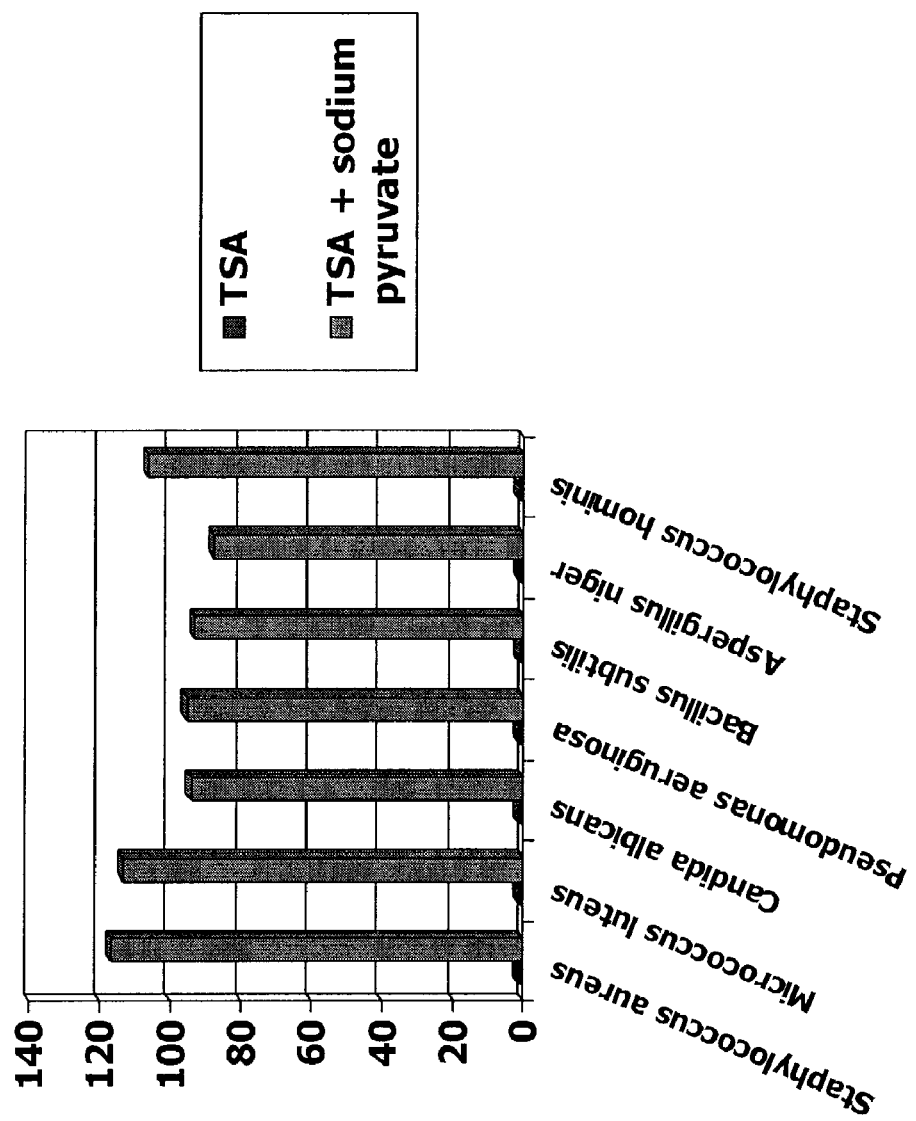
FIG. 2 represents a bar chart showing the effect of sodium pyruvate in the presence of a concentration of 8 ppm of hydrogen peroxide on the recovery level of the microorganisms.

The results obtained are shown in FIG. 2, in which the x-axis represents the nature of the microorganisms and the y-axis represents the level of recovery.

It is observed that the sodium pyruvate permits the formation and counting of colonies of microorganisms whereas the growth medium not having this does not permit the formation of colonies of microorganisms.

In addition, it is observed that the level of recovery is very good, since it is always at least 80%, whatever the microorganism considered.

EXAMPLE 4

Example 3 was reproduced by sampling 1 $m^3$ of air comprising 8 ppm of hydrogen peroxide which were impacted, firstly, on the same TSA growth medium to which 1% by weight of sodium pyruvate was added, not sterilized by the action of gamma radiation. Then, secondly, the same test was repeated but, this time, on the same growth medium sterilized by the action of gamma radiation.

Figure 3:
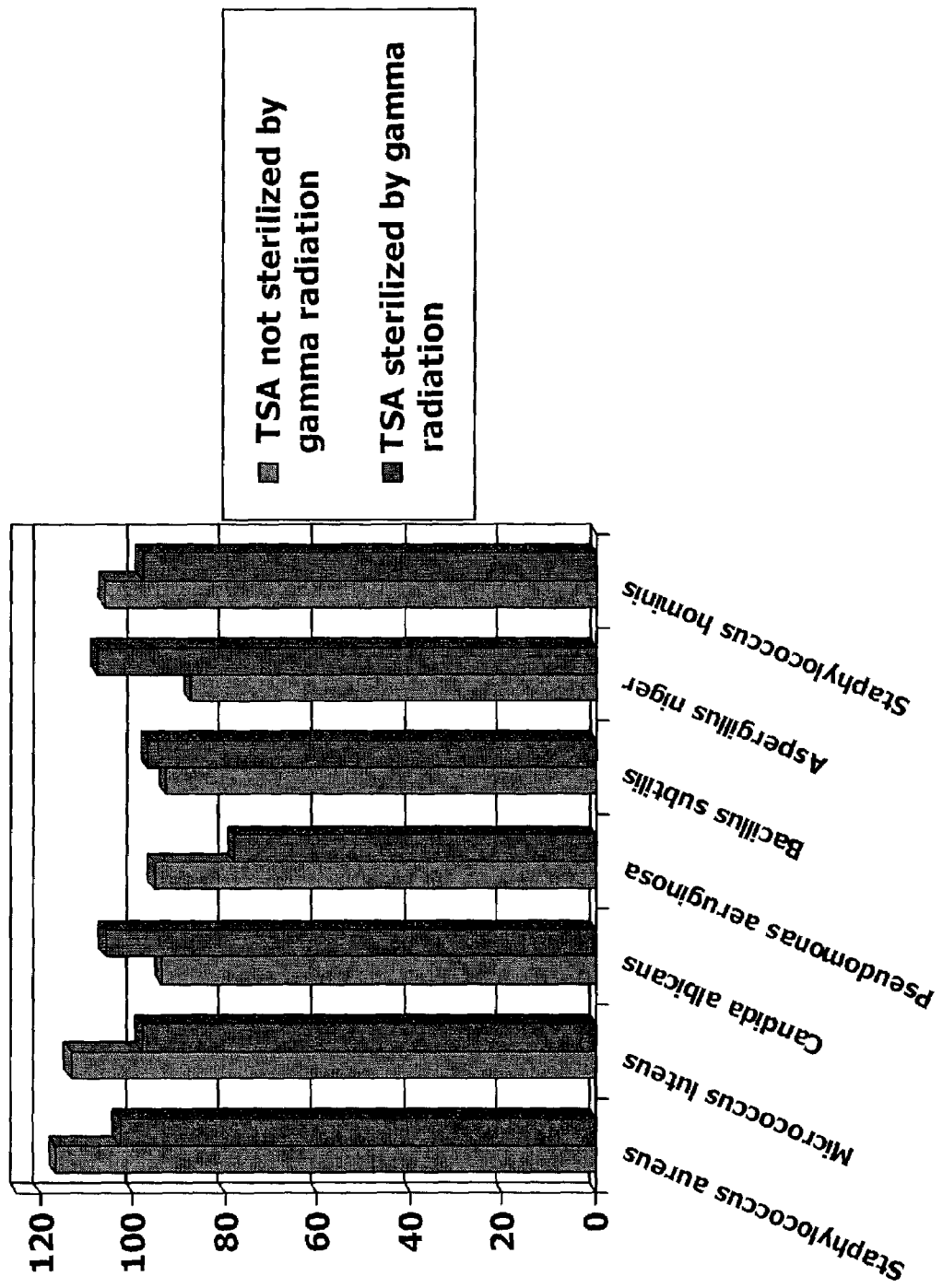
FIG. 3 represents a bar chart showing the effect of sodium pyruvate after sterilization by gamma radiation on the recovery level of the microorganisms.

The results obtained are shown in FIG. 3, in which the x-axis represents the nature of the microorganisms and the y-axis represents the level of recovery.

It may be noted that the sodium pyruvate maintains its effect whether the growth medium is sterilized or not by gamma radiation.

EXAMPLE 5

The conditions of Example 3 were reproduced using high concentrations of pyruvate ($\geq 1\%$), in the presence or absence of hydrogen peroxide in the gaseous environment.

1/ Tolerance of the microorganisms *Miccrococcus Luteus* and *Pseudomonas aeruginosa* subjected to an increasing concentration of pyruvate (test performed in the absence of hydrogen peroxide):

The recovery level of *Miccrococcus luteus* and *Pseudomonas aeruginosa* growing on TSA medium supplemented with 2.5%, 5% and 10% of pyruvate concentration, was monitored in the absence of hydrogen peroxide, using a control according to example 3.

Figure 5:
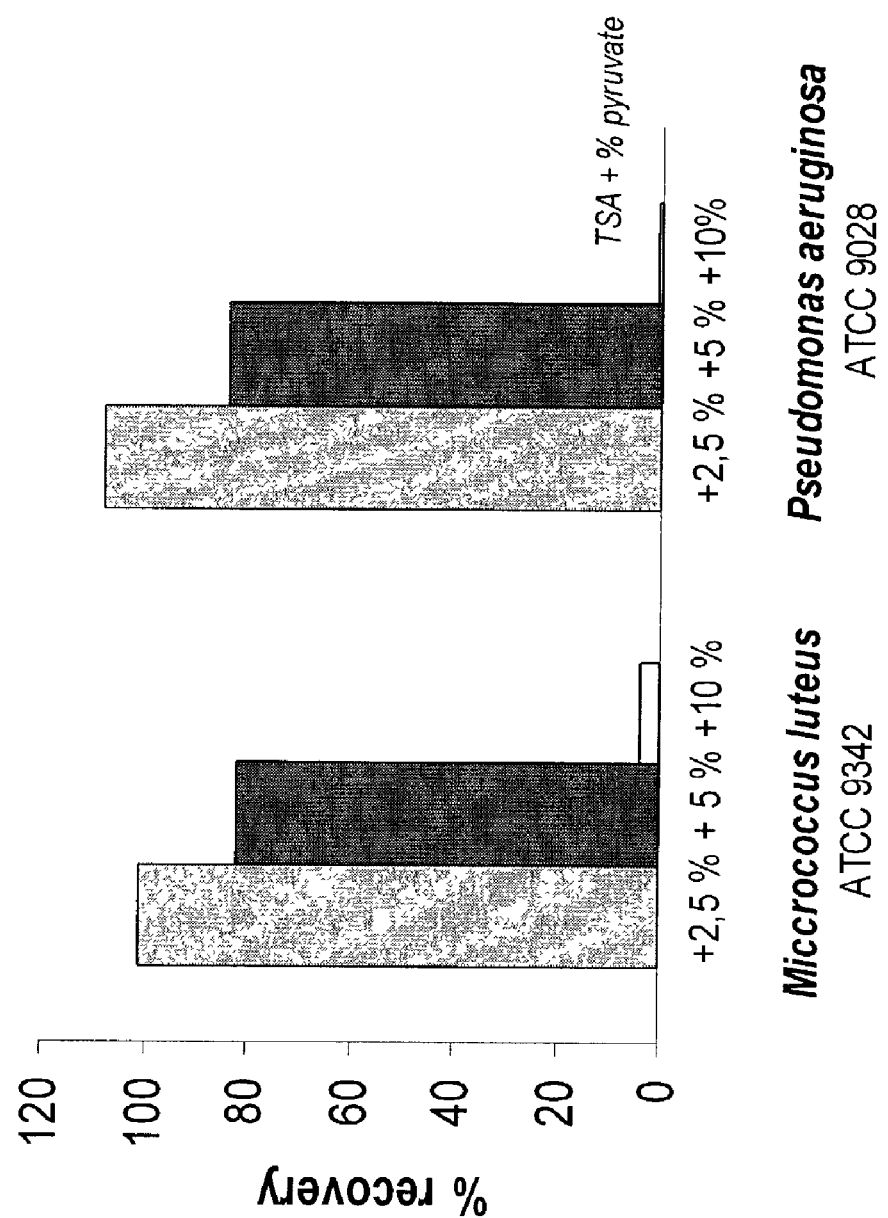
FIG. 5 represents a bar chart showing the effect of increasing pyruvate sodium weight concentration in the TSA agar growth medium from 2.5% to 10% in the absence of hydrogen peroxide, on the recovery level of the microorganisms.

The level of recovery of *Miccrococcus luteus* and *Pseudomonas aeruginosa* (% ratio) is respectively reported in the bar chart of FIG. 5, in relation with the different concentrations of pyruvate added to the agar growth medium.

In both cases, a significant inhibitory effect on *Miccrococcus luteus* and *Pseudomonas aeruginosa* recovery is observed when the pyruvate concentration passes above 5% by agar medium weight.

2/ Tolerance of the microorganisms *Miccrococcus Luteus* and *Pseudomonas aeruginosa* subjected to an increasing concentration of pyruvate in the presence of 5 to 15 ppm of hydrogen peroxide in the gaseous environment:

An experiment similar to the one described above was performed, but in the presence of an amount of hydrogen peroxide comprised between 5 and 15 ppm. The TSA agar growth medium was respectively supplemented with 1%, 2%, 3%, 4% and 5% pyruvate.

Figure 6:
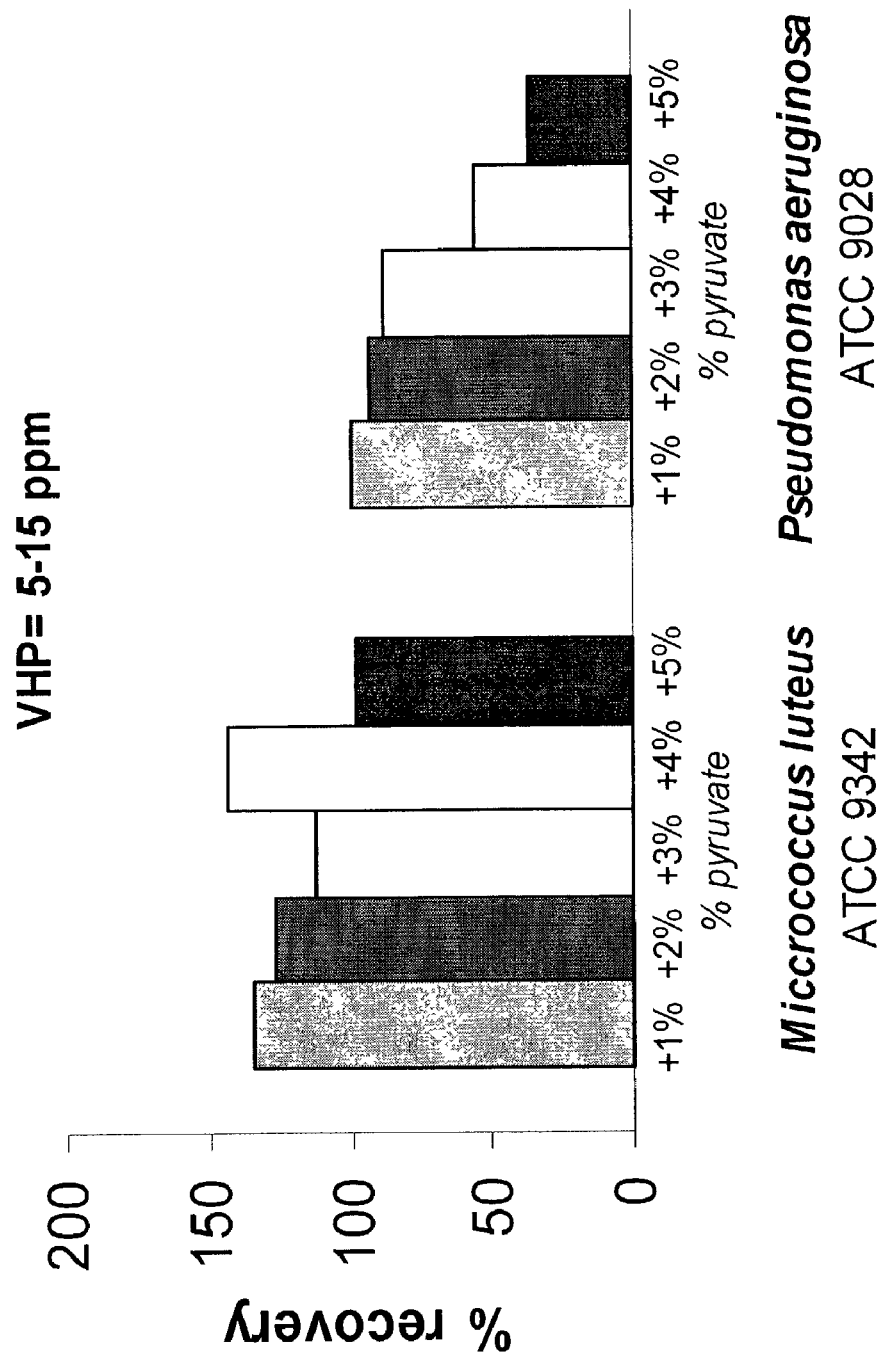
FIG. 6 represents a bar chart showing the effect of increasing pyruvate sodium weight concentration in the TSA agar growth medium from 1% to 5% in the presence of 5–15 ppm of hydrogen peroxide, on the recovery level of the microorganisms.

The level of recovery for both *Miccrococcus luteus* and *Pseudomonas aeruginosa* in each case is reported in the bar chart of FIG. 6.

3/ Tolerance of *Miccrococcus luteus* in drastic conditions, when hydrogen peroxide is raised up to 300 ppm in the gaseous environment and the concentration of pyruvate is up to 5% by weight of agar growth medium.

*Miccrococcus luteus* growth has been monitored using respectively 100 ppm and 300 ppm of hydrogen peroxide, whereas the concentration of pyruvate by weight of TSA agar growth medium was 1% and 5%.

The results obtained in these conditions are reported in table I

TABLE I

| medium | TSA | | TSA + 1% | | | TSA + 5% | | | |
| --- | --- | --- | --- | --- | --- | --- | --- | --- | --- |
| Hydrogen Peroxide (ppm) | 0 | | 100 | | 300 | | 100 | | 300 |
| colonies | Mean Nb | Mean Nb | Recovery % | Mean Nb | Recovery % | Mean Nb | Recovery % | Mean Nb | Recovery % |
| *Miccrococus luteus* ATCC9342 | 46.8 | 46 | 98 | 0 | 0 | 49 | 105 | 32.2 | 69 |

As shown in Table I, the presence of both a high concentration of hydrogen peroxide(300 ppm) and an important concentration of pyruvate (5%) enable growth of *Miccrococcus luteus*.

Altogether the results presented in Example 5, show that a high concentration of pyruvate has a strong ability to alleviate microorganism growth inhibition in the presence of high hydrogen peroxide concentrations.

Therefore, according to the present invention, it is possible to test for the presence of microorganisms in a gaseous environment comprising high levels of hydrogen peroxide.

The invention claimed is:

1. A method of testing for the presence of microorganisms in a gaseous environment or spray comprising between 15 and 400 ppm of exogenous hydrogen peroxide, wherein the following steps are implemented:
   (i) bringing the gaseous environment comprising the hydrogen peroxide into contact with an agar growth medium comprising 0.5 to 5% by weight of at least one salt of pyruvic acid;
   (ii) placing the growth medium in an environment conducive for the development of colonies of microorganisms;
   (iii) determining the presence of colonies of microorganisms which may have developed during step (ii); and
   (iv) counting the number of the colonies and/or identifying the nature of the microorganisms which make up these colonies.

2. A method according to claim 1, wherein the gaseous environment or spray further comprises ambient air.

3. A method according to claim 1, wherein the hydrogen peroxide is sprayed.

4. A method according to claim 1, wherein the content of hydrogen peroxide in the gaseous environment or spray is between 15 ppm and 300 ppm.

5. A method according to claim 1, wherein the content of hydrogen peroxide in the gaseous environment or spray is between 100 ppm and 400 ppm of hydrogen peroxide.

6. A method according to claim 1, wherein said at least one pyruvic acid salt is sodium pyruvate.

7. A method according to claim 1, wherein the agar growth medium content comprises from 1% to 5% by weight of at least one pyruvic acid salt.

8. A method according to claim 1, wherein the agar growth medium comprises from more than 1% to up to 5% by weight of at least one pyruvic acid salt.

9. A method according to claim 1, further comprising providing a flow of said gaseous environment or spray, and wherein the surface of the agar growth medium is brought into contact with said flow of said gaseous environment or spray comprising hydrogen peroxide, said flow having a substantially constant rate of flow.

10. A method according to claim 1, wherein the agar growth medium has a thickness of 5 to 8 mm.

11. A method according to claim 1, wherein the agar growth medium has a thickness of 1 to 20 mm.

12. A method according to claim 10, wherein the agar growth medium comprises from 3% to 5% by weight of at least one pyruvic acid salt.

* * * * *